US011446371B2

(12) United States Patent
Ganesh et al.

(10) Patent No.: US 11,446,371 B2

(45) Date of Patent: Sep. 20, 2022

(54) TARGETING OF LIGAND BINDING SITES IN CLFA

(71) Applicant: THE TEXAS A&M UNIVERSITY SYSTEM, College Station, TX (US)

(72) Inventors: Vannakambadi K. Ganesh, Pearland, TX (US); Magnus Hook, Houston, TX (US)

(73) Assignee: The Texas A&M University System, College Station, TX (US)

(*) Notice: Subject to any disclaimer, the term of this patent is extended or adjusted under 35 U.S.C. 154(b) by 252 days.

(21) Appl. No.: 15/773,372

(22) PCT Filed: Nov. 4, 2016

(86) PCT No.: PCT/US2016/060709

§ 371 (c)(1),
(2) Date: Aug. 21, 2018

(87) PCT Pub. No.: WO2017/079681

PCT Pub. Date: May 11, 2017

(65) Prior Publication Data

US 2018/0369355 A1 Dec. 27, 2018

Related U.S. Application Data

(60) Provisional application No. 62/251,367, filed on Nov. 5, 2015.

(51) Int. Cl.

| | |
|---|---|
| ***A61K 39/085*** | (2006.01) |
| ***C07K 16/12*** | (2006.01) |
| ***A61P 31/04*** | (2006.01) |
| ***A61K 31/4174*** | (2006.01) |
| ***A61K 31/43*** | (2006.01) |
| ***A61K 31/436*** | (2006.01) |
| ***A61K 31/496*** | (2006.01) |
| ***A61K 31/65*** | (2006.01) |
| ***A61K 39/40*** | (2006.01) |
| ***A61K 45/00*** | (2006.01) |
| ***C12N 15/00*** | (2006.01) |

(52) U.S. Cl.

CPC ........ *A61K 39/085* (2013.01); *A61K 31/4174* (2013.01); *A61K 31/43* (2013.01); *A61K 31/436* (2013.01); *A61K 31/496* (2013.01); *A61K 31/65* (2013.01); *A61K 39/40* (2013.01); *A61K 45/05* (2013.01); *A61P 31/04* (2018.01); *C07K 16/1271* (2013.01); *C12N 15/00* (2013.01); *C07K 2299/00* (2013.01); *C07K 2317/24* (2013.01); *C07K 2317/34* (2013.01); *C07K 2317/92* (2013.01)

(58) Field of Classification Search

CPC .... A61K 39/00; A61K 39/085; A61K 39/395; A61K 39/40

USPC ..... 424/9.1, 9.2, 130.1, 133.1, 139.1, 185.1, 424/234.1, 243.1

See application file for complete search history.

(56) References Cited

U.S. PATENT DOCUMENTS

| | | | | |
|---|---|---|---|---|
| 6,680,195 | B1 | 1/2004 | Patti et al. | |
| 6,841,154 | B2 | 1/2005 | Foster et al. | |
| 6,979,446 | B2 * | 12/2005 | Patti | C07K 16/1271 424/165.1 |
| 7,045,131 | B2 | 5/2006 | Patti et al. | |
| 7,115,264 | B2 | 10/2006 | Patti et al. | |
| 7,241,592 | B2 | 7/2007 | Hook et al. | |
| 7,364,738 | B2 * | 4/2008 | Patti | C07K 16/1271 424/165.1 |
| 7,381,793 | B2 | 6/2008 | Patti et al. | |
| 7,504,490 | B1 * | 3/2009 | Weinstock | C07K 14/38 435/69.3 |
| 7,666,438 | B1 | 2/2010 | Patti et al. | |
| 7,850,974 | B2 | 12/2010 | Hook et al. | |
| 7,968,100 | B2 | 6/2011 | Foster et al. | |
| 8,017,133 | B2 | 9/2011 | Patti et al. | |
| 8,377,451 | B2 | 2/2013 | Pavliak et al. | |
| 8,475,798 | B2 | 7/2013 | Patti et al. | |
| 8,759,318 | B2 | 6/2014 | Chamberlain et al. | |
| 9,351,989 | B2 | 5/2016 | McGuigan et al. | |
| 2005/0287164 | A1 | 12/2005 | Patti et al. | |
| 2007/0026011 | A1 | 2/2007 | Liu et al. | |

FOREIGN PATENT DOCUMENTS

| | | | |
|---|---|---|---|
| WO | 2003052076 | * | 6/2003 |
| WO | 2014/195280 | A1 | 12/2014 |
| WO | 2017/079681 | A1 | 5/2017 |

OTHER PUBLICATIONS

Domanski, et al. "Characterization of a Humanized Monoclonal Antibody Recognizing Clumping Factor A Expressed by *Staphylococcus aureus*" Infection and Immunity, Aug. 2005, pp. 5229-5232.

Ganesh, et al. "A Structural Model of the Staphylococcus aureus CLfA-Fibrinogen Interaction Opens New Avenues for the Design of Anti-Staphylococcal Therapeutics" PLoS Pathogens, Nov. 2008, vol. 4, Issue 11.

Ganesh, et al. "Lessons from the Crystal Structure of the *S. aureus* Surface Protein Clumping Factor A in Complex With Tefibazumab, an Inhibiting Monoclonal Antibody" EbioMedicine 13, (available online Oct. 1, 2016) 328-338.

United States Patent & Trademark Office, International Search Report and Written Opinion for PCT/US2016/060709, dated Jan. 19, 2017—12 pp.

* cited by examiner

*Primary Examiner* — Jennifer E Graser

(74) *Attorney, Agent, or Firm* — Winstead PC

(57) ABSTRACT

The present invention provides methods and compositions to reduce binding of fibrinogen to the ClfA in a gram positive bacterial infections using monoclonal antibody, a polyclonal antibody, an antigen-binding antibody fragment or a composition that specifically binds to a portion of ClfA with the sequence of SEQ ID No: 15, SEQ ID NO: 16, SEQ ID NO: 17, and SEQ ID NO: 18.

11 Claims, 7 Drawing Sheets

Specification includes a Sequence Listing.

Secondary structure comparison for ClfA and mutant ClfA PWY.

| Ligand/analyte | KD (uM) |
|---|---|
| Fg/ClfA$_{221-559}$ | 0.98 |
| Fg-D/ClfA$_{221-559}$ | 0.68 |
| GST-r/ClfA$_{221-559}$ | 4.3 |
| Fg/ClfA N3 domain | 5.9 |
| Fg-D/ClfA N3 domain | 6.9 |
| GST-r/ClfA N3 domain | 54 |

TARGETING OF LIGAND BINDING SITES IN CLFA

CROSS-REFERENCE TO RELATED APPLICATIONS

This application is a National Stage of International Application No. PCT/US2016/060709, filed Nov. 4, 2016, which claims the benefit of U.S. Provisional Application No. 62/251,367, filed Nov. 5, 2015. The contents of each of which are incorporated by reference in their entirety.

TECHNICAL FIELD OF THE INVENTION

The present invention relates generally to compositions and methods for preventing and treating human and animal diseases including caused by *Staphylococcus aureus*.

STATEMENT OF FEDERALLY FUNDED RESEARCH

Not applicable.

REFERENCE TO A SEQUENCE LISTING

The present application includes a Sequence Listing which has been submitted in ASCII format via EFS-Web and is hereby incorporated by reference in its entirety. Said ASCII copy, created on Nov. 4, 2016, is named TAMU: 2069WO_SL.txt and is 4.84 KB in size.

BACKGROUND ART

Without limiting the scope of the invention, its background is described in connection with methods of treating infection by *Staphylococcus aureus*. *S. aureus* present serious health concerns for all animals, including humans, farm livestock, and household pets. These health threats are exacerbated by the rise of strains that are resistant to antibiotic treatment. *Staphylococcus aureus* is a leading cause of severe bacterial infections in both hospital and community settings. Due to its increasing resistance to antibiotics, development of additional therapeutic strategies is required to control this pathogen. Vaccination attempts against *S. aureus* have not been successful so far and an important reason may be the pathogen's elaborate repertoire of molecules that dampen the immune response. These evasion molecules not only suppress natural immunity but also hamper the current attempts to create effective vaccines.

DISCLOSURE OF THE INVENTION

The present invention provides a pharmaceutical composition comprising a monoclonal antibody, a polyclonal antibody or an antigen-binding antibody fragment that specifically binds to a portion of ClfA (Clumping factor A) comprising: a heavy chain, a light chain with a variable region that bind at least a portion of a N3 fibrinogen binding site of the ClfA with the sequence of SEQ ID No: 15, SEQ ID NO:16, SEQ ID NO:17, and SEQ ID NO:18 to reduce binding of fibrinogen to the ClfA in a gram positive bacteria; a heavy chain, a light chain with a variable region that bind to an epitope with the sequence SEQ ID No: 15, SEQ ID NO:16, SEQ ID NO:17, and SEQ ID NO:18 that bind at least a portion of a N3 fibrinogen binding site of ClfA to reduce binding; or a composition recognizing SEQ ID NO:15, SEQ ID NO:16, SEQ ID NO:17, and SEQ ID NO:18 that bind at least a portion of a N3 binding site of the ClfA to reduce binding to additional novel ligands that utilize the N3 fibrinogen binding site. The targeted ClfA is from gram positive bacteria including but not limited to *Staphylococci, Enterococci, Streptococci, Clostridium, Listeria*, or *Bacillus*. In one embodiment, the ClfA is from *S. aureus*; and in another the ClfA comprises an IgG-like ClfA fold with two ligand binding subdomain, wherein at least one of the two ligand binding subdomain bind to the monoclonal antibody, polyclonal antibody or antigen-binding fragment. The pharmaceutical composition can further comprising one or more antibiotics. The one or more antibiotics may be but not limited to penicillin G, oxacillin, vancomycin, flucloxacillin, amoxicillin, ampicillin, antipseudomonal penicillins, methicillin, nafcillin, cloxacillin, dicloxacillin, cephalosporins, carbapenems, imipenem, meropenem, ertapenem, doripenem, tetracyclines, macrolides, fluoroquinolones, trimethoprim/sulfamethoxazole (TMP/SMX), gentamicin, vancomycin, daptomycin, telavancin, cefazolin, mupirocin, teicoplanin, tetracyclines, minocycline, doxycycline, erythromycin, rifampin, clindamycin, linezolid and aminoglycoside.

The present invention provides a medicament for the treatment of a gram positive bacterial infections comprising a monoclonal antibody, polyclonal antibody or antigen-binding antibody fragment that specifically binds to a portion of a ClfA comprising a heavy chain, a light chain with a variable region that bind at least a portion of a N3 fibrinogen binding site of the ClfA with the sequence of SEQ ID No: 15, SEQ ID NO:16, SEQ ID NO:17, and SEQ ID NO:18 to reduce binding of fibrinogen at the ClfA in a gram positive bacteria; or a heavy chain, a light chain with a variable region that bind to an epitope with the sequence SEQ ID No: 15, SEQ ID NO:16, SEQ ID NO:17, and SEQ ID NO:18 that bind at least a portion of a N3 fibrinogen binding site of the ClfA to reduce binding; or of a composition recognizing SEQ ID NO:15, SEQ ID NO:16, SEQ ID NO:17, and SEQ ID NO:18 that bind at least a portion of a N3 binding site of the ClfA to reduce binding to additional novel ligands that utilize the N3 fibrinogen binding site. The ClfA may be from *S. aureus*, alternatively the ClfA may be from but not limited to *Staphylococci, Enterococci, Streptococci, Clostridium, Listeria*, or *Bacillus*. The ClfA comprises an IgG-like ClfA fold with two ligand binding subdomain, wherein at least one of the two ligand binding subdomain bind the N3 fibrinogen binding site. The medicament may further comprise one or more antibiotics effective against the gram positive bacterial disposed in a pharmaceutical carrier. The one or more antibiotics may be but not limited to penicillin G, oxacillin, vancomycin, flucloxacillin, amoxicillin, ampicillin, antipseudomonal penicillins, methicillin, nafcillin, cloxacillin, dicloxacillin, cephalosporins, carbapenems, imipenem, meropenem, ertapenem, doripenem, tetracyclines, macrolides, fluoroquinolones, trimethoprim/sulfamethoxazole (TMP/SMX), gentamicin, vancomycin, daptomycin, telavancin, cefazolin, mupirocin, teicoplanin, tetracyclines, minocycline, doxycycline, erythromycin, rifampin, clindamycin, linezolid and aminoglycoside.

The present invention provides a medicament for the treatment of a gram positive bacterial infection to reduce binding of fibrinogen comprising a pharmacologically effective amount of a vaccine in a pharmaceutically acceptable excipient, wherein the vaccine comprises: a monoclonal antibody, a polyclonal antibody or an antigen-binding antibody fragment that specifically binds to a portion of ClfA comprising: a heavy chain, a light chain with a variable region that bind at least a portion of a N3 fibrinogen binding site of the ClfA with the sequence of SEQ ID No: 15, SEQ ID NO:16, SEQ ID NO:17, and SEQ ID NO:18 to reduce binding of fibrinogen to the ClfA in a gram positive bacteria; a heavy chain, a light chain with a variable region that bind to an epitope with the sequence SEQ ID No: 15, SEQ ID NO:16, SEQ ID NO:17, and SEQ ID NO:18 that bind at least a portion of a N3 fibrinogen binding site of ClfA to reduce binding; or a composition recognizing SEQ ID NO:15, SEQ ID NO:16, SEQ ID NO:17, and SEQ ID NO:18 that bind at least a portion of a N3 binding site of the ClfA to reduce binding to additional novel ligands that utilize the N3 fibrinogen binding site; or inhibits the interaction of fibrinogen with the ClfA in the gram positive bacterial infection; or to reduce the virulence of the gram positive bacteria. The ClfA may be from *S. aureus*, alternatively the ClfA may be from but not limited to *Staphylococci, Enterococci, Streptococci, Clostridium, Listeria*, or *Bacillus*. The ClfA comprises an IgG-like ClfA fold with two ligand binding subdomain, wherein at least one of the two ligand binding subdomain bind the N3 fibrinogen binding site. The medicament may further comprise one or more antibiotics effective against the gram positive bacterial disposed in a pharmaceutical carrier. The one or more antibiotics may be but not limited to penicillin G, oxacillin, vancomycin, flucloxacillin, amoxicillin, ampicillin, antipseudomonal penicillins, methicillin, nafcillin, cloxacillin, dicloxacillin, cephalosporins, carbapenems, imipenem, meropenem, ertapenem, doripenem, tetracyclines, macrolides, fluoroquinolones, trimethoprim/sulfamethoxazole (TMP/SMX), gentamicin, vancomycin, daptomycin, telavancin, cefazolin, mupirocin, teicoplanin, tetracyclines, minocycline, doxycycline, erythromycin, rifampin, clindamycin, linezolid and aminoglycoside.

In any of the embodiments the composition includes a peptide, a protein, a peptidomimetic, an organic composition or combination thereof that recognizes and binds to SEQ ID NO:15, SEQ ID NO:16, SEQ ID NO:17, and SEQ ID NO:18.

The present invention provides a method of determining the presence of gram positive bacteria in a test sample, comprising the steps of: providing a test sample; contacting the test sample with a monoclonal antibody, polyclonal antibody or antigen-binding antibody fragment that specifically binds to a portion of a ClfA comprising a heavy chain, a light chain with a variable region that bind at least a portion of a N3 fibrinogen binding site of the ClfA with the sequence of SEQ ID No: 15, SEQ ID NO:16, SEQ ID NO:17, and SEQ ID NO:18, or a heavy chain, a light chain with a variable region that bind to an epitope with the sequence SEQ ID No: 15, SEQ ID NO:16, SEQ ID NO:17, and SEQ ID NO:18 that bind at least a portion of a N3 fibrinogen binding site; and a detectable label; and detecting the presence of gram positive bacteria in the test sample based on the signal generated by the detectable label, wherein the presence of gram positive bacteria is directly correlated with the signal generated by the detectable label. The ClfA may be from *S. aureus*, alternatively the ClfA may be from but not limited to *Staphylococci, Enterococci, Streptococci, Clostridium, Listeria*, or *Bacillus*. In some embodiments the test sample is a patient sample and the gram positive bacteria is *Staphylococcus* and the method further comprises correlating the presence of *Staphylococcus* in the test sample, wherein and diagnosing a patient with a staphylococcal infection.

The present invention provides a method for preventing or reducing the severity of gram positive bacteria-associated sepsis in a patient, comprising the steps of administering the pharmaceutical composition as disclosed and/or claimed to a patient to prevent or reduce the severity of gram positive bacteria-associated sepsis. The present invention provides a method of delaying the onset of sepsis associated with gram positive bacterial infections in a patient, comprising the steps of administering the pharmaceutical composition as disclosed and/or claimed to delay the onset of sepsis associated with gram positive bacterial infections. The present invention provides a method of preventing the onset of sepsis associated with gram positive bacterial infections in a patient, comprising the steps of administering the pharmaceutical composition as disclosed and/or claimed to a patient to prevent the onset of sepsis associated with gram positive bacterial infection. The present invention provides a method of reducing gram positive bacterial load in the bloodstream or heart in a patient comprising the steps of administering the pharmaceutical composition as disclosed and/or claimed to a patient to reduce a gram positive bacterial load in the bloodstream or heart. The present invention provides a method of reducing gram positive bacterial agglutination and/or thromboembolic lesion formation in a patient comprising the steps of administering the pharmaceutical composition as disclosed and/or claimed to a patient to reduce gram positive bacterial agglutination and/or thromboembolic lesion formation. The present invention provides a method of preventing gram positive bacterial infections in a patient comprising the steps of administering the pharmaceutical composition as disclosed and/or claimed to a patient to prevent gram positive bacterial infections in a patient. An additional step to any of these methods includes the step of providing one or more antibiotics and the one or more antibiotics may be selected from but not limited to penicillin G, oxacillin, vancomycin, flucloxacillin, amoxicillin, ampicillin, antipseudomonal penicillins, methicillin, nafcillin, cloxacillin, dicloxacillin, cephalosporins, carbapenems, imipenem, meropenem, ertapenem, doripenem, tetracyclines, macrolides, fluoroquinolones, trimethoprim/sulfamethoxazole (TMP/SMX), gentamicin, vancomycin, daptomycin, telavancin, cefazolin, mupirocin, teicoplanin, tetracyclines, minocycline, doxycycline, erythromycin, rifampin, clindamycin, linezolid and aminoglycoside. In any of the methods disclosed herein, the gram positive bacteria may be *Staphylococcus*; the gram positive bacteria may be *S. aureus*; the gram positive bacteria may include but not limited to *Staphylococci, Enterococci, Streptococci, Clostridium, Listeria*, or *Bacillus*. The ClfA may be from *S. aureus*.

DESCRIPTION OF THE DRAWINGS

For a more complete understanding of the features and advantages of the present invention, reference is now made to the detailed description of the invention along with the accompanying figures and in which:

FIG. 1A is a graph of $ClfA_{221-559}$ binding to Tefibazumab. FIG. 1B is a graph of $IC_{50}$ measurements for the inhibition of Tefibazumab on $ClfA_{221-559}$ binding to immobilized Fg and D-fragment (Fg-D). FIG. 1C is a SPR sensorgram showing Tefibazumab binding to $ClfA_{221-559}$ and $ClfA_{CC}$ surfaces.

FIG. 3A is an image of a ribbon diagram of ClfA-N3 domain showing the positions of PWY residues. FIG. 3B illustrates biacore sensorgrams showing $ClfA_{221-559}$ and its variants binding to immobilized Tefibazumab and fibrinogen.

FIG. 3C shows ITC measurement of $ClfA_{PWY}$ and Fg-γ P16 peptide interaction.

DESCRIPTION OF EMBODIMENTS

Figure 1A:
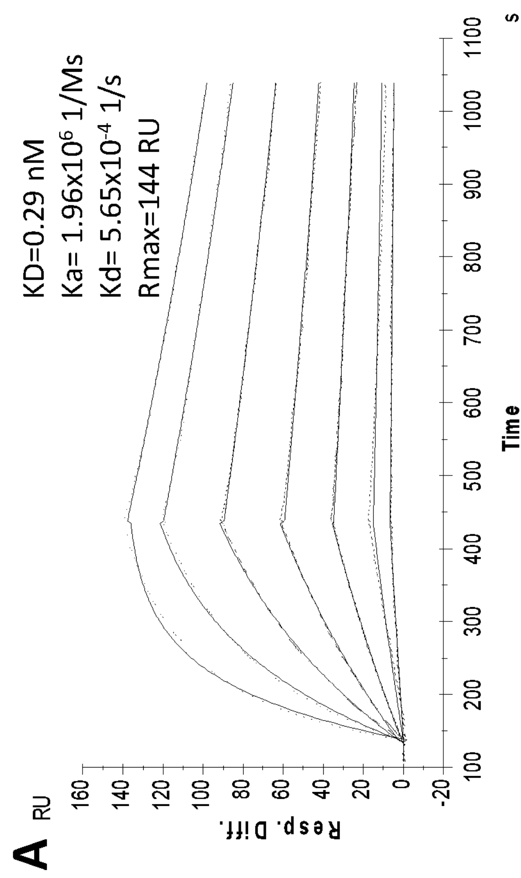
FIGS. 1A-1C illustrate the interaction of Tefibazumab with ClfA.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "MSCRAMM" denotes a Microbial Surface Components Recognizing Adhesive Matrix Molecule.

As used herein the term "composition" denotes a composition that is a peptide, a protein, a peptidomimetic, an organic composition or combination thereof that recognizes and binds to SEQ ID NO:15, SEQ ID NO:16, SEQ ID NO:17, and SEQ ID NO:18. This can be a drug, small organic compound, polymer, macromolecule, biological molecule, protein, peptide or other structure that recognizes and binds to SEQ ID NO:15, SEQ ID NO:16, SEQ ID NO:17, and SEQ ID NO:18.

The present invention describes the crystal structure of ClfA:Tefibazumab which provides a structural model of the ClfA:Tefibazumab interaction. The structural model is further used to understand (1) mechanism of action by Tefibazumab, (2) determination of amino acid residue positions on ClfA involved in the interaction with Tefibazumab (3) generate atomic models of ClfA-ligand/mAb or inhibitory peptides or small molecules (4) screening novel inhibitor compounds.

The crystal structure revealed that the Tefibazumab epitope overlaps a previously unknown fibrinogen binding site in ClfA (N3 fibrinogen binding site) and not at the known fibrinogen (Fg) γ-peptide binding sites (N2 N3 fibrinogen binding site) on ClfA. The mechanism of action of Tefibazumab therefore must involve interfering with this previously unknown secondary Fg interaction site. Further molecular modeling suggested an Fg binding site that partially overlaps with the Tefibazumab binding site. This present Invention discloses the presence of this second synergistic host ligand binding site located on the N3 domain (N3 fibrinogen binding site) of ClfA. Targeting the ligand interactions sites in MSCRAMMs are key for inhibitor design strategies to generate effective therapeutic agents. The structure of Tefibazumab in complex with ClfA identify the residues in the MSCRANLVI representing the epitope of an inhibiting mAb and as such represents the basis for constructing mAbs or mAb based molecules targeting this epitope.

*S. aureus* is a potent, opportunistic human pathogen that has evolved in a symbiotic relationship with its hosts and is notorious for its ability to cause a variety of infections, ranging from relatively mild skin infections to life threatening diseases such as sepsis, pneumonia and endocarditis and is responsible for more death in the United States than any other microbe including HIV. Due to the rapid emergence of antibiotic resistant strains, novel preventive and therapeutic strategies are being explored; however, at least nine phase HMI clinical trials have failed to reduce the rate of *S. aureus* infections. An important reason for these failures may be the bacteria's ability to evade even an enhanced host's defense systems. Inducing the formation of a protective Fg containing shield to evade the hosts defensive strategies. ClfA is known to bind the carboxy terminal of the γ-chain of Fg, a region that is important for platelet aggregation and coagulation and recombinant ClfA has been reported to inhibit the interaction of Fg with the platelet integrin $\alpha_{IIb}\beta_3$. However, the virulence potential of ClfA does not appear to correlate with altered platelet aggregation or Fg coagulation in a mouse model of septicemia but seems to be a function of impaired bacterial clearance. In fact ClfA can protect *S. aureus* against phagocytosis by macrophages and it appears that Fg plays an important role in the ClfA mediated inhibition of phagocytosis. Mouse models have shown that ClfA is a critical virulence factor in *S. aureus* infections and removal of the gene encoding ClfA through gene manipulation results in significant loss of virulence potential. Furthermore introducing the gene encoding ClfA into a bacterial species that otherwise is apathogenic results in a new bacteria capable of killing the mouse.

ClfA is an MSCRAMM (Microbial Surface Components Recognizing Adhesive Matrix Molecules) that bind the C-terminus of Fg γ-chain for their initial interactions. The present inventors discovered that ClfA also engages a novel unexpected secondary synergistic site located "on top" of the N3 subdomain. This is confirmed from solving a structure of ClfA. N2N3 in complex with a blocking mAb (Tefibazumab) that binds on top of N3. Furthermore, the present inventors identified the epitope on ClfA N3 for Tefibazumab. Blocking the second Fg binding site on top on N3 thus prevents the formation of a Fg shield induced by CIfA, which is required for vaccines and immunotherapeutics to be effective. The family of surface anchored proteins, called MSCRAMMs, has a common stnictural organization where the N-terminal half is composed of three domains N1, N2 and N3. Many MSCRANLMs including ClfA bind host molecules by DLL (Dock, Lock and Latch) mechanism, which involves a site between the N2 and N3 domains of the MSCRAMM (N2N3 site). ClfA interacts with the carboxy terminal of the γ-chain of Fibrinogen (Fg) termed, γ-peptide by a variant of the DLL mechanism.

Tefibazumab (also known as AUREXIS™) is a high affinity humanized monoclonal antibody (mAb) specific to ClfA that has been studied in a phase I and II clinical trials in humans. Tefibazumab effectively inhibits ClfA binding to Fg but the mechanism of action was previously unknown. The present inventors discovered that the crystal structure of CIfA in complex with a Fab fragment of Tefibazumab and surprisingly and unexpectedly, the Tefibazumab binding site and the known Fg γ-peptide binding sites (N2N3 site) do not overlap. The mechanism of inhibition of Tefibazumab therefore must involve interfering with a previously unknown secondary Fg interaction site. Further molecular modeling suggested an Fg, binding site that partially overlaps with the Teflbazumab binding site. This present Invention discloses the presence of this second synergistic host ligand binding site located on the N3 domain (N3 Site) of ClfA. The structure of Tefibazumab in complex with ClfA identify the residues in the MSCRANLM representing the epitope of an inhibiting mAb and as such represents the basis for constructing mAbs or mAb based molecules with enhanced properties.

The present invention has located an Fg binding site which overlaps with the Tefibazumab binding epitope. The present invention includes a structural model of the ClfA: Tefibazumab interaction, which can be used in the design and generation of more effective therapeutic mAbs. The therapeutic agent of the present invention may be antibodies, biologics, peptides, peptide fragments, organic compounds, inorganic compounds and other organic molecules and modified monoclonal antibodies that binds to the epitope on Clfa defined by Tefibazumab and reduces the binding of fibrinogen to ClfA. The present invention includes therapeutic agents and compositions related to Tefibazumab and similar molecules.

The structure of an MSCRAMM:mAb complex helped to identify a new location in ClfA that can be targeted for therapeutic intervention; provided clues for the presence of a second synergistic fibrinogen binding site (N3 site), for ligand on ClfA and the novel aspects are in A area: (1). *S. aureus* assembles an Fg containing shield to protect itself from clearance. Effective vaccines and immuno-therapeutics need to prevent the shield from forming or disrupt the shield in order to be effective. (2) The binding of Fg to ClfA and related MSCRAMMs requires two sites. (3) The second synergistic site located on top of N3 might be more suitable as a target for interference.

The invention includes vaccine components that include the two binding sites but does not bind Fg with high affinity. Due to the importance of ClfA as a virulence factor, the protein has been explored as a potential vaccine candidate. Recombinant ClfA induced an antibody response in mice and mice immunized with ClfA presented with less severe arthritis compared to mice immunized with a control antigen. Moreover, passive immunization with polyclonal ClfA antibodies (Abs) generated in rats or rabbits protected mice against *S. aureus* induced sepsis and arthritis. A combination therapy of vancomycin with high titers of human polyclonal Abs or a monoclonal antibody (mAb) against ClfA was protective in a catheter induced infective endocarditis model in rabbits where treating with vancomycin alone was less effective.

In the present inventors determined the crystal structure of $ClfA_{CC}$ in complex with a Fab fragment of Tefibazumab. The co-crystal structure revealed an unexpected binding site for Tefibazumab on "top" of the N3 domain of ClfA. This mAb binding site is distinct from the trench between N2 and N3 where the Fg peptide ligand docks and suggests that residues outside the docking trench on ClfA are important for Fg binding. Further biochemical studies confirm the presence of a second binding site on top of N3 that is critical for a high affinity Fg/ClfA interaction. These results reveal that Tefibazumab inhibits ClfA binding to Fg by targeting a second Fg binding site on the MSCRAMM and provide additional target sites for future design of effective inhibitors of the ClfA/Fg interaction.

Bacterial strains, plasmids and primers. Amino acid substitutions in the Tefibazumab epitope of ClfA were generated in the plasmid pQE30 vector expressing $ClfA_{229-545}$ from *S. aureus* strain Newman by site-directed mutagenesis using the primers listed in Table 1 below. $ClfA_{221-559}$ was expressed using plasmids described earlier. Alternatively, pCF41 (carrying DNA encoding residues 221-559 of ClfA served as template for introducing $Y_{512A}$, $P_{467A}$ and $W_{518A}$ substitutions. Overlapping complementary primers containing the desired nucleotide changes were used to amplify the plasmid using and Phusion polymerase were used to amplify the plasmid as per the manufacturer's instructors (Thermo Scientific).

TABLE 1

| SEQ ID NO: | Primer designation | Primer (5'-3') |
|---|---|---|
| | | $ClfA_{229-545\,(Q429K)}$ |
| 1 | Forward | GTAATGCATTAATAGATCAGA**AA**AATACAAGTAT |
| 2 | Reverse | CTGATCTATTAATGCATTACTATCCGTATTT |
| | | $ClfA_{229-545\,(S461Q)}$ |
| 3 | Forward | ACTTTGAGGATGTCACTAAT**CAG**GTGAATATTAC |
| 4 | Reverse | ATTAGTGACATCCTCAAAGTTTTCTGGATTC |
| | | $ClfA_{229-545\,(N463R)}$ |
| 5 | Forward | AGGATGTCACTAATAGTGTG**CG**TATTACATTCCC |
| 6 | Reverse | CACACTATTAGTGACATCCTCAAAGTTTTCT |
| | | $ClfA_{229-545\,(N515R)}$ |
| 7 | Forward | CTTTATATGGGTATAACTCGCG**T**ATAATTTGGCG |
| 8 | Reverse | CGAGTTATACCCATATAAAGTTGAACGTAAA |
| | | $ClfA_{221-559\,(P467A)}$ |
| 9 | Forward | GAATATTACATTC**GC**AAATCCAAAT |
| 10 | Reverse | GATTTGGATTTG**C**GAATGTAATATTG |
| | | $ClfA_{221-559\,(y512A)}$ |
| 11 | Forward | GTTATACCCAGTTAAAG**CA**GAACGTAAAG |
| 12 | reverse | CTTTACGTTC**TG**CTTTAACTGGGTATAAC |
| | | $ClfA_{221-559\,(W518A)}$ |
| 13 | Forward | GAATATAATT**GC**GCGCTCTATGTC |
| 14 | Reverse | GACATAGAGCGC**GC**AATTATATTC |

The PCR reaction was incubated with 1U of the restriction enzyme Dpnl (New England Biolabs) for 1 hour at 37° C. to digest methylated DNA used as template and transformed into *E. coli* TG1 (Zymo Research). Primers were synthesized by Sigma-Aldrich. *E. coli* was grown at 37° C. in Luria-Bertani (LB) broth supplemented with 100 μg/ml of ampicillin (Sigma-Aldrich). Plasmids were extracted with Wizard Plus SV Minipreps DNA purification system (Promega) and the mutation was confirmed by DNA sequencing (Genewiz).

Recombinant proteins. The recombinant proteins were expressed in *E. coli* Topp3 (Bayou Biolabs) and purified by nickel chelate chromatography and anion exchange chromatography as previously described. GST tagged γ-peptide were expressed and purified as described earlier.

Generation of Fab Fragments. Purified Tefibazumab (a generous gift of Inhibitex, Inc.) was dialyzed against 20 mM sodium phosphate pH 7.0 and concentrated to ~2 ml volume with a final concentration of ~10 mg/ml. Beads containing immobilized papain (Thermo Scientific, Rockford, Ill.) were washed 3 times with phosphate buffer and a 50% slurry was made with the digestion buffer, 20 mM phosphate, 20 mM cysteine, 10 mM EDTA, pH 7.0. Prior to starting the digestion, cysteine was also added to the mAb solution to a final concentration of 20 mM. Five hundred μl of slurry was added to the 2 ml sample and the mixture was incubated for 8 hours at 37° C. The papain beads were then removed by centrifugation and the digest was dialyzed against phosphate buffer. Subsequently undigested IgG and generated Fc fragments were removed by passing the mixture through a protein A column (Thermo Scientific, Rockford, Ill.).

Crystallization, Structure Solution and Refinement. The isolated Fab fragments were mixed with purified $ClfA_{CC}$ at an equal molar ratio and left for 1 hour at 4° C. The complex was then concentrated to ~10 mg/ml for crystallization experiments. Two μl of the sample was mixed with 2 μl of reservoir solution containing PEG 4000, 2% isopropanol, 0.1 M Hepes pH 7.0 and allowed to equilibrate in a limbro plate at 4° C. Several crystals were collected, washed 3 times with stabilizing solution, then dissolved and run on an SDS-page gel to confirm the presence of both proteins. The X-ray data was measured on a Rigaku RAXIS $IV^{++}$ for 240 degrees with an oscillation width of 1°. Data was processed using the d*trek software suite. The structure was solved by the molecular replacement (MR) method using $ClfA_{CC}$ (pdbid; 1VR3) as the search model. To determine the MR solution for the Fab fragment, several poly-alanine models of Fv fragments from the PDB database were attempted of which pdb id; 1F8T yielded a reasonable MR solution. The model was rebuilt using Coot and refined using CNS and Refmac 5.0 to a final R-factor of 24% and an R free of 29%. The data collection and refinement statistics are summarized in Table 2.

TABLE 2

Crystallographic data measurement and refinement data

| | ClfA:Tefibazumab |
|---|---|
| Cell dimensions | |
| a, b, c (Å) | 234.2, 84.4, 48.0 |
| β (°) | 99.07 |
| Space group | C2 |
| Max Resolution (Å) | 2.4 |
| Reflections unique | 34583 |
| Completeness (%) | 99.5 (99) |
| $R_{merge}$* | 0.9 |
| Number of molecules in the asymmetric unit | 1 |
| Rfactor/$R_{free}$⁺ | 0.206/0.299 |
| Average B value (Å) | 72 |
| No of non-hydrogen atoms | 6030 |
| ClfA | 2427 |
| Tefibazumab | 3168 |
| Water | 417 |
| Rms deviations from ideal values | |
| Bond lengths (Å) | 0.022 |
| Bond Angles (°) | 1.95 |

*$R_{merge} = \Sigma \mid I_j - \langle I \rangle \mid / \Sigma I_j$; where $I_j$ is the measured and <I> is the mean intensity of reflection hkl ⁺$R_{free}$ is calculated over 5% of randomly selected reflections not included in the refinement Isothermal Titration calorimetry. To determine a $K_D$ for the Fg/ClfA interaction, soluble Fg (Enzyme Research Laboratories, South Bend, Ind.) and $ClfA_{CC}$ was co-dialyzed with 10 mM HEPES; 150 mM NaCl; pH 7.4 and analyzed by isothermal titration calorimetry (ITC) using a VP-ITC microcalorimeter (MicroCal). The cell contained 7 μM Fg and the syringe contained 150 μM $ClfA_{CC}$ after all samples had been degassed for 5 minutes. The titration was performed at 30° C. using a preliminary injection of 5 μl followed by 29 injections of 10 μl with an injection speed of 0.5 μl/sec and a stirring speed of 260 rpm. Since Fg is a dimeric molecule, a single binding model with 14 μM concentration of Fg was used for data fitting and analyzed using Origin version 5 software (MicroCal). For performing ITC for $ClfA_{PWY}$/P16 peptide interactions, samples of 0.5 mM P16 peptide were injected into a cell containing 30 μM of $ClfA_{PWY}$. P16 is a variant of Fg γ-chain containing a D410A amino acid substitution. The titration was performed at 30° C. using a preliminary injection of 5 μl followed by 29 injections of 10 μl with an injection speed of 0.5 μl/sec.

Surface Plasmon Resonance. Surface plasmon resonance-based binding experiments were performed at 25° C. on a Biacore 3000 (GE Healthcare/Biacore, Uppsala, Sweden). Phosphate buffered saline (PBS-T: 8.06 mM $Na_2HPO_4$, 1.94 mM $KH_2PO_4$, 2.7 mM KCl and 137 mM NaCl, pH 7.4, and 0.005% Tween-20) was used as running buffer for immobilization and binding experiments. Flow rate of 5 μl/min was used during immobilization and a higher rate 30 or 50 μl/min for binding experiments. The fibrinogen (Fg) surface was prepared on a CM5 sensor chip via standard amine-coupling chemistry. A Fg solution (10 μl of 20 μg/ml in sodium citrate, pH5.5) was injected to an activated (4 min) flow cell. After deactivation, about 7000 resonance units (RU) of Fg were immobilized. A reference surface was prepared with activation and deactivation steps but no protein coupled. To prepare a capturing surface for Tefibazumab, about 3000 RU of goat anti-Human IgG (Fc) polyclonal $F(ab')_2$ (Pierce) were immobilized using 10 μg/ml of $F(ab')_2$ resuspended in 10 mM sodium acetate pH5.0. For GST fusion protein capturing, approximately 11000 RU of goat anti-GST antibody (GE Healthcare/Biacore) were immobilized simultaneously on two flow cells on a CM5 sensor chip. GST-tagged Fg γ-peptide (20 μg/ml in PBS-T) was captured by the antibody and created a ligand surface (about 700 RU). The other flow cell with GST captured (about 900 RU) served as a reference surface. To regenerate the ligand surfaces, bound proteins were removed by a 1 minute injection of 1 M NaCl for the Fg surface, 10 mM glycine pH 2.6 for Tefibazumab surface, and 0.01% SDS for the Fg γ-peptide surface. All SPR responses were baseline corrected by subtracting response generated from reference surface.

Figure 1B:
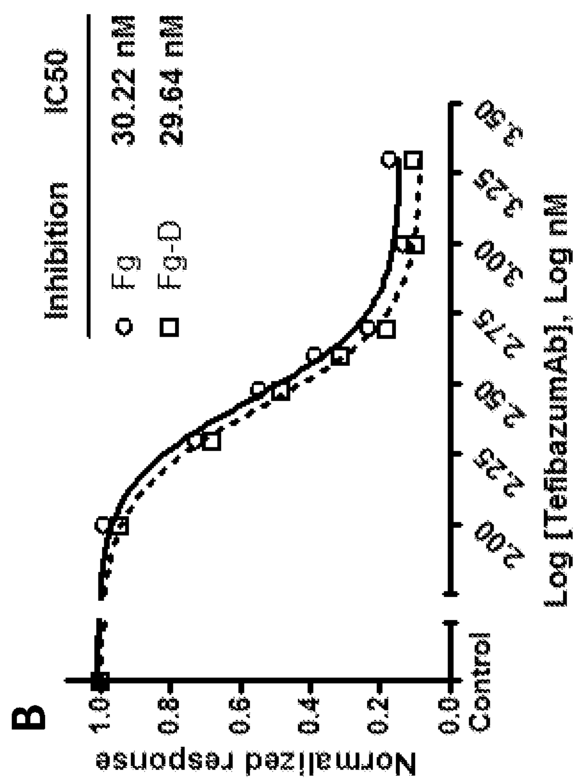
Figure 1C:
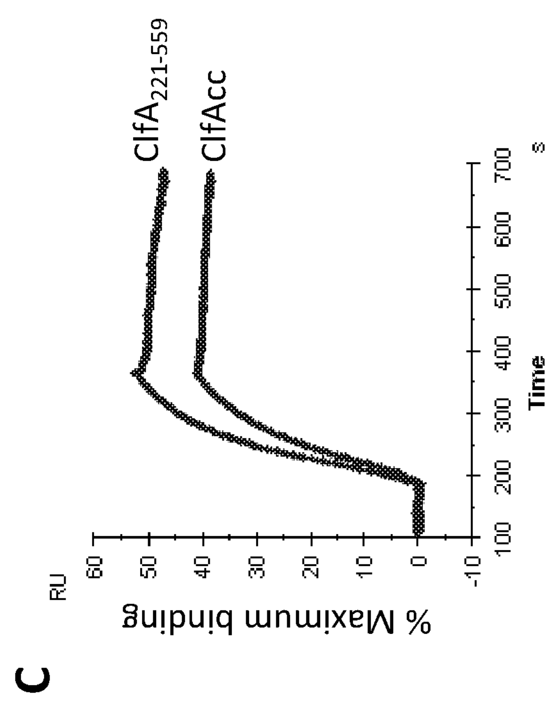

FIGS. 1A-1C are images of SPR analysis of the interaction of Tefibazumab with ClfA. FIG. 1A is a graph of $ClfA_{221-559}$ (0.05-6.4 nM) binding to Tefibazumab (600 RU captured by rabbit anti-mouse Fc IgG). FIG. 1B is a graph of IC50 measurements for the inhibition of Tefibazumab (0.1 to 2 μM) on 1 μM of $ClfA_{221-559}$ binding to immobilized Fg and D-fragment. There is no detectable direct binding of Tefibazumab (up to 2 μM) to the Fg surfaces (data not shown). FIG. 1C is a graph of SPR sensorgrams showing Tefibazumab (3 nM) binding to $ClfA_{221-559}$ and $ClfA_{CC}$ surfaces. Tefibazumab binds to different forms of ClfA. The mAb 12-9 was raised in mice using $ClfA_{221-559}$ from *S. aureus* strain Newman as the antigen and was previously shown to bind to $ClfA_{40-559}$ (subdomains N1N2N3) containing A-region of ClfA with high affinity. Analysis of Tefibazumab (the humanized form of 12-9) binding to $ClfA_{221-559}$ and its effect on the ClfA/Fg interaction by SPR confirmed that the mAb binds to $ClfA_{221-559}$ with high affinity ($K_D$=0.29 nM; FIG. 1A) and, under the experimental conditions used, inhibited $ClfA_{221-559}$ binding to immobilized human Fg or the Fg D-fragment with an IC50 value of 30 nM for either target (FIG. 1B). Earlier structural and biochemical studies showed that a shorter closed variant of the MSCRAMM, $ClfA_{CC}$, also effectively bound to Fg. In $ClfA_{CC}$ two Cys residues (D327C/K541C) have been introduced to form a disulfide bond and keep the latch in the latching trench. Since the subdomain orientation of $ClfA_{221-559}$ and $ClfA_{CC}$ are different as revealed by the corresponding crystal structures to determine if Tefibazumab recognizes both forms of ClfA N2N3. The SPR sensorgrams (FIG. 1C) showed that Tefibazumab bound almost identically to both $ClfA_{221-559}$ and $ClfA_{CC}$.

Crystal structure of the ClfA/Tefibazumab Fab complex. To uncover the structural basis for the ability of Tefibazumab to inhibit ClfA binding to Fg and to determine the epitope on ClfA recognized by the mAb we attempted to crystallize ClfA:N2N3 in complex with a Fab fragment of Tefibazumab. The Fab fragment of Tefibazumab was generated by digesting the mAb with immobilized papain and cleared by passing the digest through an immobilized protein A column to remove undigested Abs and Fc containing antibody fragments. Since Tefibazumab binds to $ClfA_{CC}$ we used this more stable form of the MSCRAMM in the crystallization experiments. Different crystallization screens were initially performed for the MSCRAMM/Fab fragment. The conditions described in Materials and Methods were used to generate large crystals suitable for X-ray analyses. The crystals diffracted X-rays to a 2.6 Å resolution and the structure of the complex was solved by the molecular replacement method.

Figures 2A, 2B, 2C:
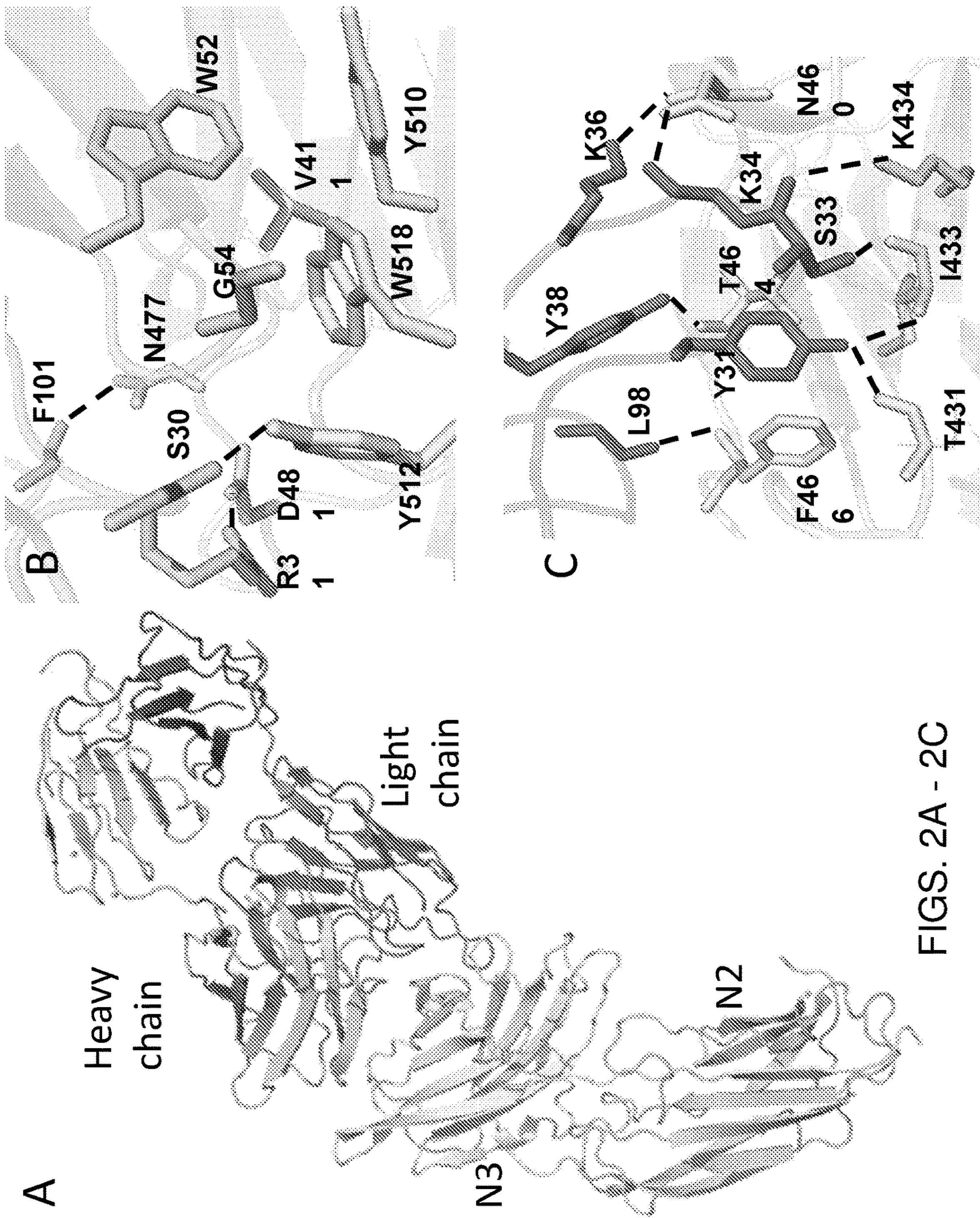
FIGS. 2A-2C are structural images of ClfA-Tefibazumab interactions.

FIGS. 2A-2C are images of ClfA-Tefibazumab interactions. (FIG. 2A) The structure of disulfide bond-closed $ClfA_{CC}$ in complex with the Fab fragment of Tefibazumab. $ClfA_{CC}$ N2 and N3 domains are shown in green and yellow, respectively. The light and the heavy chains of the Fab fragment are shown in magenta and cyan, respectively. (FIG. 2B) Hydrogen bonding and key interactions between ClfA and the heavy chain of Tefibazumab. Hydrogen bonds are shown in dotted lines. ClfA residues are shown in yellow and heavy chain residues are shown in cyan. (FIG. 2C) Hydrogen bonding and key interactions between ClfA and the light chain of Tefibazumab. Hydrogen bonds are shown in dotted lines. ClfA residues are shown in yellow and light chain residues are shown in magenta. The overall structure of the complex is shown in FIG. 2A.

As expected, $ClfA_{CC}$ was found in the latch-closed form due to the presence of the engineered disulfide bond. The overall structure of ClfA in the complex is similar to the structure observed in the $ClfA_{CC}$/Fg γ-peptide complex with an rms deviation of 0.54 Å for 306 Cα atoms. The Tefibazumab Fab binds only to the ClfA N3 domain making it unlikely that the mAb could affect N2-N3 subdomain orientations (FIG. 2*a*) consistent with the SPR data showing that Tefibazumab (FIG. 1C) binds equally well to $ClfA_{221-559}$ and $ClfA_{CC}$. Furthermore, the overall structure of the N3 subdomain in the Fab/$ClfA_{CC}$ complex is similar to the structures of the N3 subdomain in other ClfA structures and show rms deviations of 0.4 Å and 0.3 Å with the apo-$ClfA_{221-559}$ and $ClfA_{CC}$/Fg γ-peptide structures, respectively. Thus the binding of the Fab fragment to ClfA does not seem to induce any significant conformational change in the MSCRAMM. Furthermore, the binding site of Tefibazumab is "on top" of the N3 subdomain where the mAb would not affect the redirection of the N3 C-terminal extension in $ClfA_{221-559}$ including the locking and latching events. These conclusions are consistent with the experimental data showing that the mAb binds to the closed form of $ClfA_{CC}$. The Fab/MSCRAMM complex in total buries a solvent associable area of 1834 $Å^2$ (ClfA:879 $Å^2$, Fab:955 $Å^2$) with the light chain burying more surface area than the heavy chain.

TABLE 3

List of hydrogen bonds in the ClfA:Tefibazumab interactions. The donor $^{(D)}$ and acceptor $^{(A)}$ atoms are shown in parenthesis:

| Heavy Chain | | | Light Chain | | |
|---|---|---|---|---|---|
| ClfA | mAb | Distance (A°) | ClfA | mAb | Distance (A°) |
| Y 512(OH)$^D$ | S 30(O)$^A$ | 2.37 | I 433(N)$^D$ | Y 31(OH)$^A$ | 3.05 |
| D 481(OD2)$^A$ | R 31(NH1)$^D$ | 2.10 | T 431(O)$^A$ | Y 31(OH)$^D$ | 2.60 |
| N 477(ND2)$^D$ | F 101(O)$^A$ | 2.84 | I 433(O)$^A$ | S 33(OG)$^D$ | 2.84 |
| | | | K 434(NZ)$^D$ | S 33(O)$^A$ | 3.14 |
| | | | N 460(OD1)$^D$ | N 34(O)$^A$ | 2.76 |
| | | | N 460(O)$^A$ | K 36(NZ)$^D$ | 2.91 |
| | | | T 464(O)$^A$ | Y38(OH)$^D$ | 2.67 |
| | | | F 466(N)$^D$ | L 98(O)$^A$ | 3.06 |

The Tefibazumab epitope. The ClfA/Fab heavy chain interaction. The interaction between ClfA and Tefibazumab is predominantly hydrophobic in nature with only 3 hydrogen bonds between the heavy chain and ClfA (FIG. 2B, Table 3). A view of the ClfA/Fab heavy chain interactions is shown in FIG. 2B. The side chains of Tyr512 and Asp481 of ClfA form hydrogen bonds with residues in the CDR1, back-bone carbonyl oxygen "O" of Ser30 and the side chain of Arg31(NH1), respectively. In addition, Asn477 participates in a hydrogen bond with backbone oxygen (O) of Phe101. Surface exposed Trp518 of ClfA stacks with the backbone of Gly54 of the heavy chain. Trp52 of CDR2 docks in a hydrophobic pocket formed by Val411, Trp518 and Tyr510 of ClfA. In addition, a significant number of hydrophobic residues that are surface exposed in the apo structure are masked by the interaction with the Fab. Masking of a large patch of a hydrophobic surface could be responsible for the high affinity that Tefibazumab shows for ClfA. The Tefibazumab epitope. The ClfA/Fab light chain interaction. The interaction of ClfA with the light chain of Tefibazumab is primarily hydrophilic in nature and is shown in FIG. 2C. In total eight hydrogen bonds help stabilize the light chain/$ClfA_{CC}$ interactions (FIG. 2C, Table 3). The long CDR1 of the light chain makes extensive contact with ClfA with seven hydrogen bond interactions. Tyr31 (CDR1) is involved in two hydrogen bonds with the backbone atoms of Ile433 and Thr431 of ClfA. Ser33, Lys36, and Tyr38 (CDR1) interact with carbonyl oxygens of Ile433, Asn460 and Thr464 in ClfA, respectively. In addition, Lys434 and Asn460 of ClfA contact the backbone atoms of Ser33 and Asn34 of CDR1, respectively, through hydrogen bonds. The interaction with CDR3 is less extensive with one backbone-backbone hydrogen bond between Phe466 (ClfA) and Leu98 (CDR3). There is no contact between CDR2 of the light chain and ClfA within 4.0 Å cut-off distance. A list of all residues in ClfA and Tefibazumbab Fab making contact (within a 4 Å cut off distance) is shown in Table 4.

TABLE 4

Tefibazumab binding epitope on ClfAN2N3. The positions of residues in the N3 domain of ClfA are labeled. Light chain variable domain (VL) makes extensive contact with the strands D and D' and the loop (D-D' loop) joining the two strands.

| Light chain | | Heavy chain | |
|---|---|---|---|
| Residue | Position | Residue | Position |
| Q 428 | C-D loop | I 408 | C strand |
| T 431 | | V 411 | |
| | | D 468 | D' strand |
| | | K 473 | |
| S 432 | D strand | N 477 | D''-E loop |
| I 433 | | D 481 | |
| K 434) | | Y 510 | F strand |
| | | Y 512 | |
| N 460 | D-D' Loop | W 518 | G strand |
| T 464 | D' Strand | | |
| T 465 | | | |
| F 466 | | | |
| P 467 | | | |

Biochemical characterization of the Tefibazumab epitope. To confirm the structural model of the ClfA/Tefibazumab complex derived from the diffraction data we made several substitutions in the ClfA N3 domain at the Tefibazumab epitope identified above and evaluated the mAb MSCRAMM interaction by SPR (FIG. 3A).

Figure 3A:
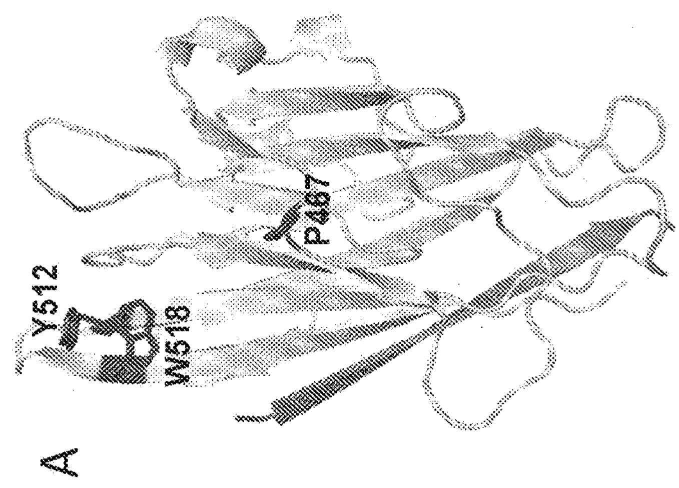
FIGS. 3A-3C show the effect of the ClfA N3 domain mutants on the binding of ClfA to Tefibazumab and Fg.
Figure 3B:
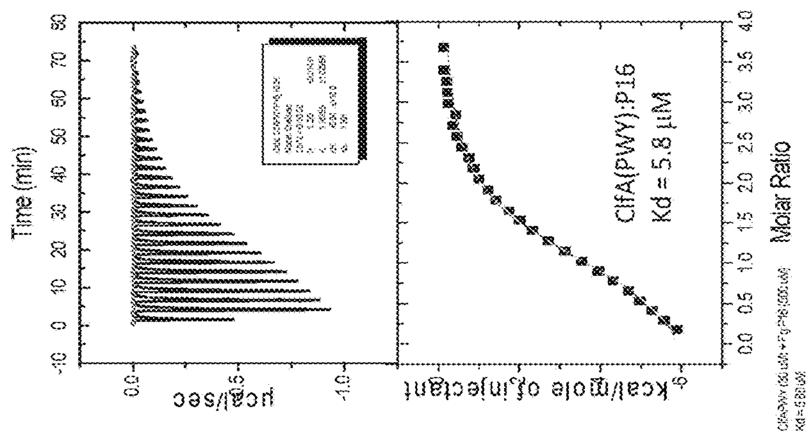
Figure 3C:
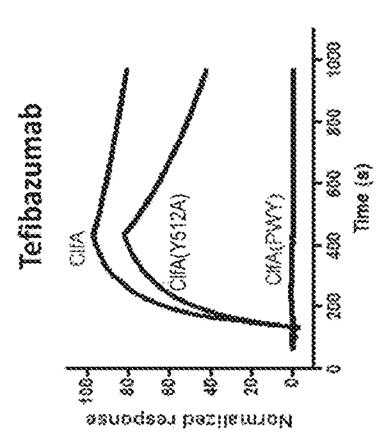

FIGS. 3A-3C illustrate the effect of the ClfA N3 domain mutants on the binding of ClfA to tefibazumab and Fg. FIG. 3A is a ribbon diagram of ClfA-N3 domain showing the positions of PWY. The Fg γ-peptide is shown as a ribbon to show the location of the Fg γ-peptide binding site. FIG. 3B is a graph of biacore sensorgrams showing 0.1 μM of $ClfA_{221-559}$ and its variants binding to immobilized Tefibazumab and fibrinogen. The amino acid substitutions in the variant proteins were made at the mAb binding site. FIG. 3C is a graph of $ClfA_{PWY}$ and Fg-γ P16 peptide interaction measured by ITC. A single mutant involving changing Tyr512 in the F-strand of the N3 subdomain to Ala (Y512A) resulted in a slightly reduced binding to Tefibazumab, while a triple mutant ($ClfA_{PWY}$) comprising P467A, Y512A and W518A substitutions almost completely abolished Tefibazumab binding to $ClfA_{221-559}$ (FIG. 3B). All three residues are surface exposed and circular dichroism spectra (FIG. 4) of the wild-type ClfA ($ClfA_{WT}$) and $ClfA_{PWY}$ mutant proteins were essentially identical indicating that the substitutions had not introduced any gross changes in secondary structure.

Figure 4:
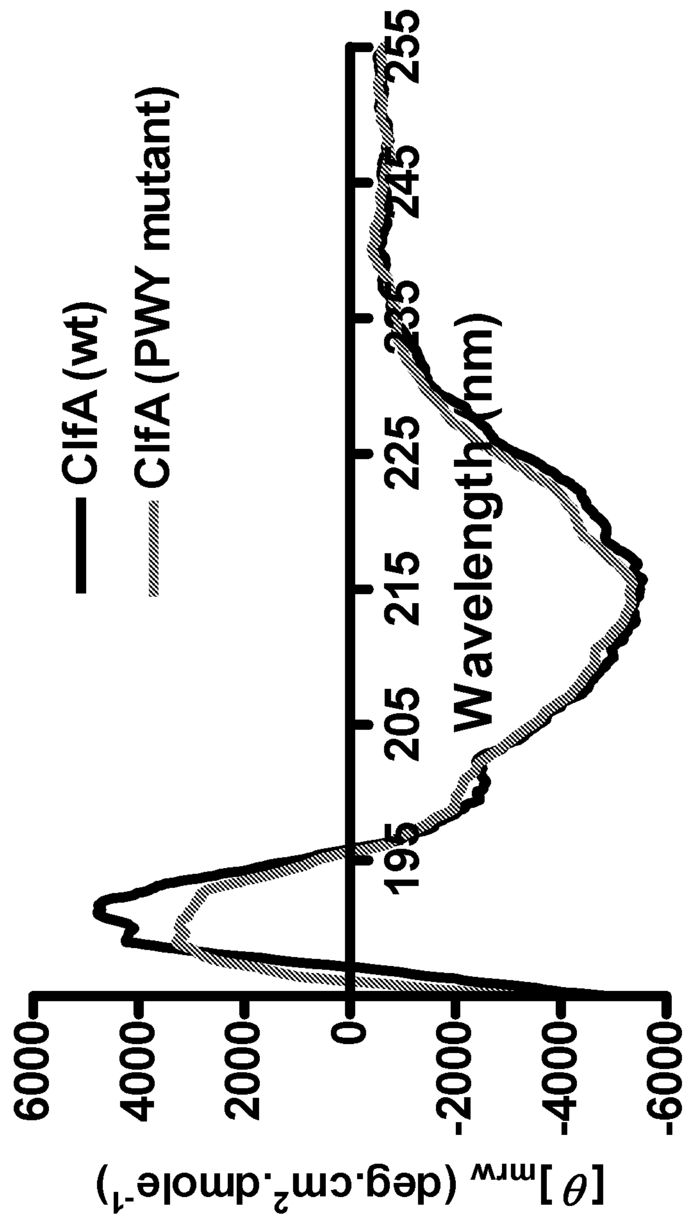
FIG. 4 is a graph of a secondary structure comparison for ClfA and mutant $ClfA_{PWY}$.

FIG. 4 is an image of the secondary structure comparison for ClfA and mutant $ClfA_{PWY}$.

TABLE 5

Buried residues in N3 subdomain of ClfA in the ClfA:Tefibazumab complex that defines the Tefibazumab epitope. The N3 subdomain (Residue 408-518) has been subdivided into 4 segments SEQ ID NO: 15-18. SEQ ID NO: 15, 16, 17 and 18

| Residue number | Residue |
|---|---|
| 408 | Ile |
| 409 | Ala |
| 411 | Val |
| 413 | Thr |
| 428 | Gln |
| 429 | Gln |
| 431 | Thr |
| 432 | Ser |
| 433 | Ile |
| 434 | Lys |
| 459 | Thr |
| 460 | Asn |
| 461 | Ser |
| 462 | Val |
| 463 | Asn |
| 464 | Ile |
| 465 | Thr |
| 466 | Phe |
| 467 | Pro |
| 471 | Gln |
| 473 | Lys |
| 475 | Glu |
| 477 | Asn |
| 478 | Thr |
| 479 | Pro |
| 480 | Asp |
| 481 | Asp |
| 510 | Tyr |
| 512 | Tyr |
| 516 | Ile |
| 518 | Trp |

SEQ ID NO: 15 $IA_XV_XT$ wherein $_X$ is any amino acid residue.
SEQ ID NO: 16 $QQ_XTSIK$ wherein $_X$ any amino acid residue.
SEQ ID NO: 17 TNSV NITFP $_{XXX}Q_X$ $K_XE_XN$ TPDD wherein $_X$ any amino acid residue.
SEQ ID NO: 18 $Y_XY_{XX}$ $_XI_XW$ wherein $_X$ any amino acid residue.

Figure 5A:
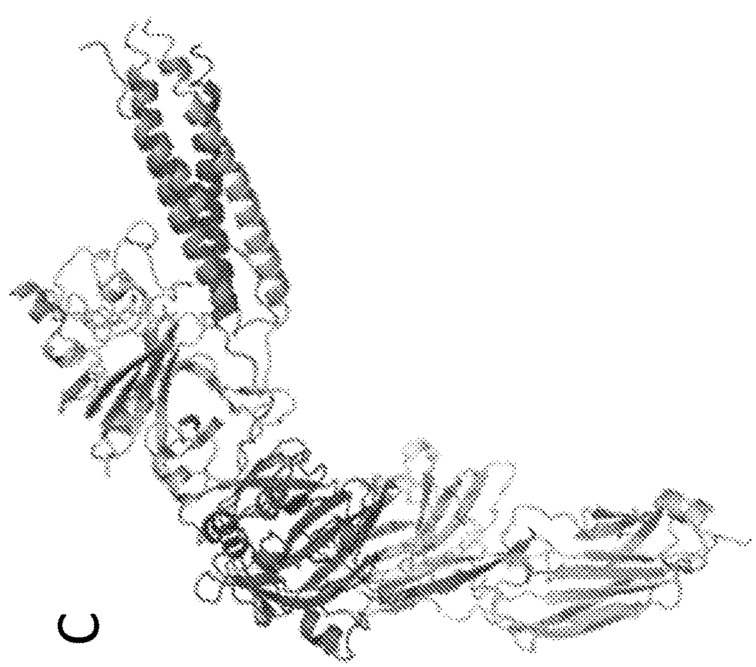
FIGS. 5A-5C are images of crystal structures of ClfACC/Fg γ-peptide and the ClfACC-Tefibazumab Fab complex and a model of ClfA-Fg interactions.
Figure 5B:
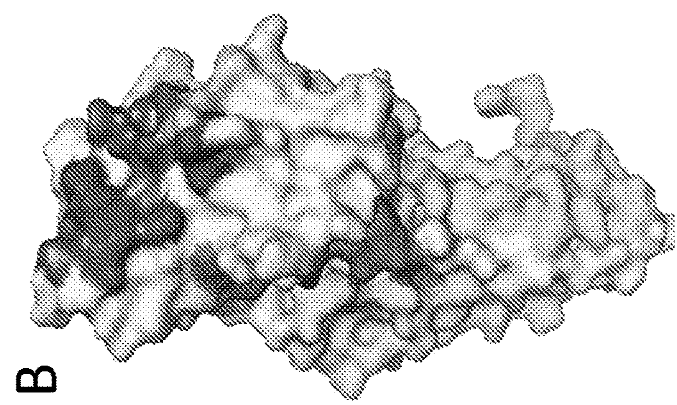
Figure 5C:
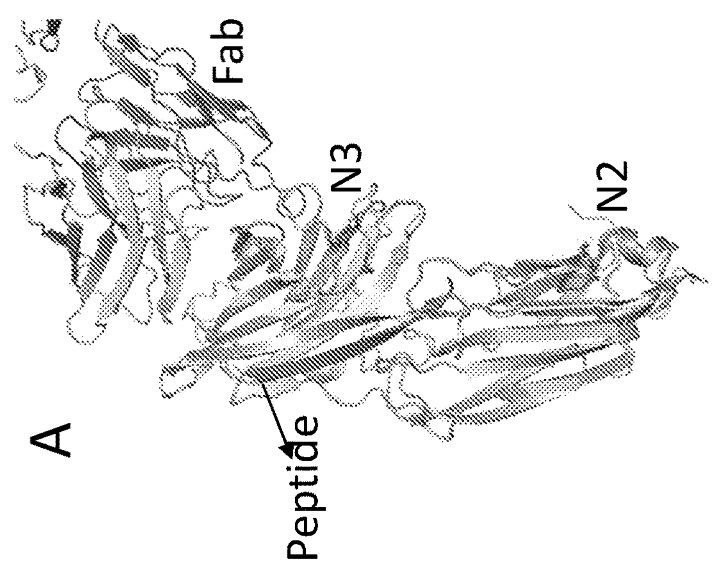

FIGS. 5A-5C include overlay of crystal structures of $ClfA_{CC}$/Fg γ-peptide and the $ClfA_{CC}$-Tefibazumab Fab complex and a model of ClfA-Fg interactions. FIG. 5A is an image of the N2 and the N3 subdomains of ClfA and Fab complex and ClfA from the Fg γ-peptide complex (PDB: 2VR3). Note that the N2N3 site and the second site do not overlap. FIG. 5B shows molecular surface representation of ClfA (N2 domain and N3 domain. The surface that contacts Fg γ-peptide and the light chain and heavy chains of Tefibazumab are shown. FIG. 5C shows molecular Molecular model of ClfA-Fg D-fragment interaction.

Superposition of the $ClfA_{CC}$/γ-peptide ligand complex and the ClfA/Tefibazumab Fab (inhibitor) complex is shown in FIG. 5A. The peptide binding site is located between the N2 and the N3 subdomains and extends along the "G" strand of N3 while the Tefibazumab epitope is found on "top" of N3 (FIG. 5A and FIG. 5B) and does not overlap with the peptide binding site. Since Tefibazumab effectively inhibits the ClfA/Fg interaction it is possible that the interaction of ClfA with Fg extends beyond the C-terminal section of Fg γ-chain and that ClfA makes additional contacts with Fg. In fact a synthetic Fg γ-peptide, even at high concentrations, can only reduce Fg binding to ClfA by a maximum of ~50% supporting a more involved model of Fg/ClfA binding. Tefibazumab may inhibit ClfA binding to Fg by blocking a potential second binding site. Four additional pieces of evidence support a binding model with multiple contact sites between Fg and ClfA.

Molecular modeling of ClfA/Fg D-fragment. The possibility of multiple contacts between ClfA and Fg was first evaluated by molecular modeling studies. As Tefibazumab inhibits ClfA binding to both Fg and the D-fragment in an almost identical way (FIG. 1B), and the affinity of ClfA for Fg and the D-fragment are very similar (see below), it is likely that all ClfA/Fg contacts involve only the D-fragment. We therefore used the crystal structures of the Fg D-fragment (Pdb id: 2H43) and $ClfA_{CC}$ for the modeling studies. The 17-residue C-terminal peptide of the Fg γ-chain, which binds to ClfA in the N2N3 trench, is a short disordered region and cannot be detected in the crystal structure of the ~80 kDa D-fragment. Rigid body docking of the D-fragment on ClfA resulted in a model of ClfA/D-fragment where the orientation of the C-terminal residue (H400) of the γ-chain in the D-fragment structure is close to the N-terminal residue (L392) of the γ-peptide in the ClfA/peptide structure. Molecular modeling showed that the docking of the C-terminal of the Fg γ-chain in the trench between the N2 and N3 subdomains could place the 30 kDa γ-globular module of the D-fragment close to the top face of the N3 domain of ClfA. In this model there is a substantial contact area between the D-fragment and the N3 domain of ClfA. Thus it is clear from the model that multiple interactions involving the N3 domain of ClfA are sterically possible when the Fg γ-peptide is docked in the N2N3 trench.

Recombinant ClfA domains can bind to intact Fg or the Fg D-fragment with significantly higher affinities than to the Fg γ-peptide. A binding mechanism involving multiple contact sites in Fg with ClfA should result in a significant increase in the affinity of the MSCRAMM for full-length Fg or the Fg D-fragment compared to the Fg γ-peptide. An ITC experiment using full-length Fg in the cell and titrating in $ClfA_{CC}$ gave a $K_D$ of 300 nM (FIG. 5A) whereas a synthetic C-terminal γ-chain peptide was titrated into a cell containing $ClfA_{CC}$ gave a $K_D$ of 9 μM (FIG. 5B). The 30-fold higher affinity observed for full-length Fg is consistent with a model involving additional contacts between ClfAN2N3 and intact Fg and that these secondary sites contribute to the higher affinity.

SPR experiments where ClfA N2N3 ($ClfA_{221-559}$) was run over chips containing immobilized intact Fg, Fg D-fragment or GST-γ-peptide showed a similar but less pronounced (about 4-7 fold) difference in $K_D$ for binding of the MSCRAMM to the γ-peptide and the Fg or Fg D-fragment, respectively. On the other hand the calculated Kd values for ClfA binding to intact Fg and Fg D-fragment, respectively, are essentially identical, 0.98 μM for Fg compared to 0.68 μM for D-fragment (FIG. 3C). Since most of the known and putative Fg interactive sites in ClfA are located within the N3 subdomain we examined the interactions of a recombinant form of N3 ($ClfA_{370-559}$) to the different forms of immobilized Fg. $Clf_{370-559}$ bound to all forms of Fg albeit with lower affinities that those observed for $ClfA_{221-559}$. The $K_D$ values recorded for $ClfA_{370-559}$ binding to Fg and Fg D-fragment were similar (FIG. 3C) and about 10-fold lower than that observed for $ClfA_{370-559}$ binding to the γ-peptide. Taken together the results of these binding studies are consistent with our model proposing additional Fg binding site(s) located in the top of the N3 subdomain and further suggest that all ClfA interactive sites in Fg are located in the D-fragment.

Mutants (or Amino acid substitutions) in the Tefibazumab epitope in ClfA affect Fg binding but not the Fg γ-peptide binding by the DLL mechanism. Tefibazumab inhibits the binding of ClfA to Fg by competing for a putative second Fg binding site on the MSCRAMM. Substitution of residues in the Tefibazumab epitope may affect Fg binding to ClfA. Consequently we examined the Fg binding of ClfA mutants ($ClfA_{Y512A}$ and $ClfA_{PWY}$) that were affected in mAb binding (FIG. 3A). SPR analysis using immobilized human Fg showed that the Y512A ClfA mutant exhibited reduced binding to Fg (FIG. 3B). The effect of the Y512A substitution was much more pronounced when Fg rather than Tefibazumab was the ligand indicating that Tyr512 plays a more important role for Fg binding than for mAb binding. The triple mutant $ClfA_{PWY}$ completely lost its ability to bind Tefibazumab and showed minimal binding to Fg (FIG. 3B). We predicted that substitution of residues located at the top of the N3 domain would not affect the binding of ClfA to the Fg γ-peptide.

Figures 6A, 6B, 6C:
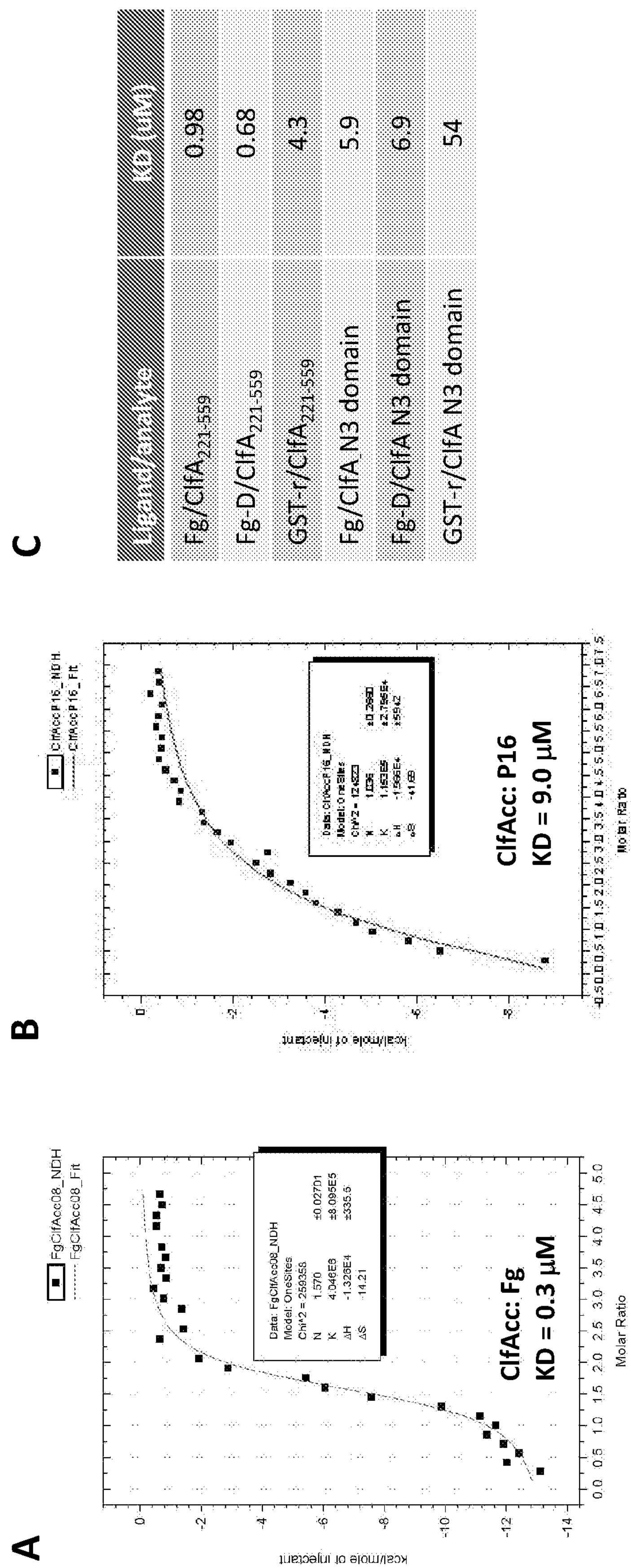
FIGS. 6A-6C are images comparing ClfA-Fg interactions.

FIGS. 6A-6C show a comparison of ClfA-Fg interactions. FIG. 6A shows detection of the interaction using ITC. Fg was placed in the cell and $ClfA_{CC}$ was titrated. FIG. 6B shows SPR analysis of the interactions between ClfA and Fg fragments. Biacore sensorgrams showing$ClfA_{221-559}$ binding to immobilized Fg and Fg-D-fragment. At nanomolar concentration range of $ClfA_{221-559}$, the binding to the GST-γ-peptide cannot be determined (ND). ITC was used to explore if the $ClfA_{PWY}$ mutant has retained the ability to bind the Fg γ-peptide P16 (FIG. 6C). P16 bound $ClfA_{PWY}$ with a similar affinity ($K_D$~5.8 μM) to that previously recorded for P16 binding to $ClfA_{221-545}$ ($K_D$=3.0 μM). In addition, SPR analysis estimated that the $K_D$ for $ClfA_{PWY}$ binding to Fg and the D-fragment to be in the low micromolar range (10 μM and 17 μM, respectively, data not shown) comparable to the Fg γ-peptide binding to ClfA (4.3 μM, Fig. FIG. 6C). These results suggest that the DLL mechanism of Fg binding remains intact in the $ClfA_{PWY}$ mutant and that the $ClfA_{PWY}$ mutant specifically lost the second Fg binding site.

Figure 7:
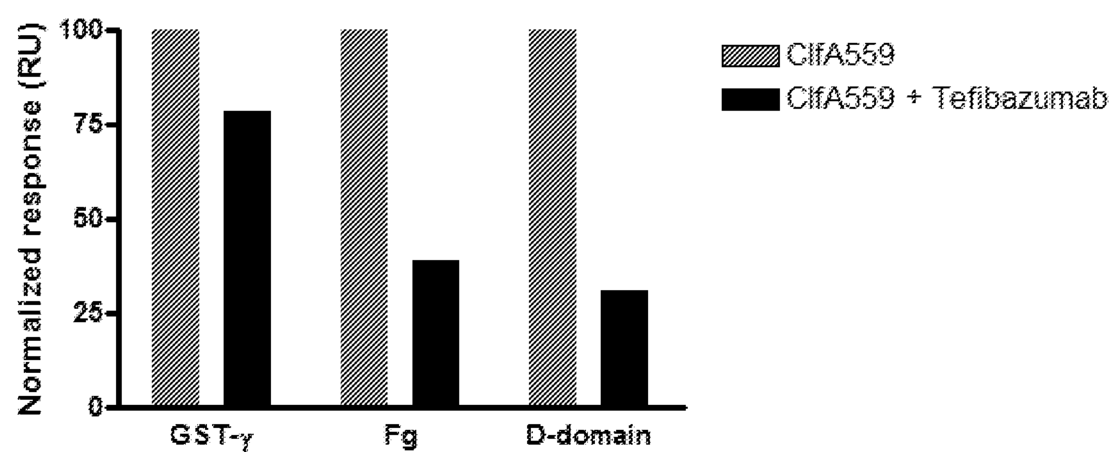
FIG. 7 is a graph of the effect of Tefibazumab on ClfA binding to immobilized Fg, D-fragment and GST-γ-peptide.

FIG. 7 is a graph showing the effect of Tefibazumab on ClfA binding to immobilized Fg, D-fragment and GST-γ-peptide. Shown here are Biacore experiments for 1 μM $ClfA_{221-559}$ in the presence (black) or absence (grey) of 2 μM Tefibazumab binding to Fg, Fg D-fragment and GST-γ-peptide surface. Tefibazumab does not inhibit the Fg γ-peptide binding to ClfA. If only the second Fg binding site but not the DLL binding is affected by Tefibazumab we would not expect binding of the Fg γ-peptide to ClfA to be affected by the mAb. To evaluate this hypothesis, we used SPR analysis of Tefibazumab-mediated inhibition of ClfA binding to immobilized GST-tagged Fg γ-peptide, the Fg D-fragment or intact Fg (FIG. 6). With higher molar ratio (Tefibazumab/ClfA=2:1) Tefibazumab could efficiently inhibit ClfA binding to Fg (about 60%) and D-fragment (about 70%), but only slightly inhibited GST-tagged Fg γ-peptide (about 25%). Taken together these results demonstrate that Tefibazumab inhibits Fg binding by blocking a second binding site at the top of the N3 domain which is distinct from the γ-peptide binding site located in the trench between the N2N3 subdomains.

The epitope for Tefibazumab to our surprise is located on top of the N3 subdomain on ClfA. Examining the sequence of the epitope region in available ClfA sequences revealed several variants. Furthermore Tefimbazumab showed a reduced affinity for at least some of these variants. Strains expressing these variant ClfA sequences likely would not be recognized and therefore the bacteria was not cleared efficiently by Tefibazumab during the clinical trial perhaps explaining why the clinical trial did not show efficacy.

Our earlier study showed that ClfA binding to Fg involves a variant of the Dock, Lock and Latch mechanism where the C-terminus of the Fg γ-chain docks in a trench formed between the N2 and N3 subdomains of the MSCRAMM. In the current report, we demonstrate that the high affinity interaction of ClfA with intact Fg involves additional contacts between the MSCRAMM and the ligand protein. These additional interactions dramatically increase the overall affinity of the interaction and may involve residues in the γ-globular domain of the γ-chain of Fg that for sterical reasons can be brought into close contact with the "top" of the N3 domain according to our modeling experiments.

The more complex binding mechanism used by ClfA to bind intact Fg could result in previously unrecognized conformational changes in Fg and could possibly mask other biological hot spots on Fg in addition to the C-terminal Fg γ-chain that is required for $\alpha_{IIb}\beta_3$ platelet integrin binding. In addition, it is possible that sequence variations in the MSCRAMM in the second binding site could affect the affinity for Fg and thus the virulence potential of the ClfA variant. Furthermore, it is possible that amino acid variations in Fg sequences in humans targeting the second site may bind with different affinities to the MSCRAMM and consequently affects the susceptibility of an individual to staphylococcal infections. It should be pointed out that the study reported here has been conducted with a segment of ClfA and it is unclear if Fg binding to the full-length MSCRAMM can involve even more extensive interactions outside the N2N3 sub-domains.

Our studies with Tefibazumab have also revealed a novel inhibitory mechanism of the binding of ClfA to Fg. Clearly Tefibazumab can only block some of the interaction sites between Fg and ClfA yet the overall effect on Fg binding to ClfA is dramatic. It is clear that the mechanism by which ClfA binds Fg is much more complex than previously appreciated and this complexity can at least partly explain the difficulty in generating effective anti-ClfA therapeutic agents including mAbs that can efficiently recognize natural ClfA variants from different stains of *S. aureus*. However, a further characterization of the second binding site(s) may provide the opportunity to designing antigens and agents that interfere with both Fg-binding sites on ClfA to effectively inhibit this interaction that is critical for *S. aureus* virulence (Josefsson et al., 2008).

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The invention claimed is:

1. A method of determining the presence of gram positive bacteria in a test sample, comprising the steps of: providing a test sample; contacting the test sample with an antibody that specifically binds to a portion of a N3 fibrinogen binding site of Clumping factor A protein (ClfA), wherein the N3 fibrinogen binding site is selected from the group consisting SEQ ID No: 15, SEQ ID NO:16, SEQ ID NO:17, and SEQ ID NO:18, wherein the binding of the antibody to the N3 fibrinogen binding site reduces binding of fibrinogen to the ClfA, and wherein the antibody contains a detectable label; binding the gram positive bacteria to the antibody; and detecting the presence of gram positive bacteria in the test sample based on the signal generated by the detectable label, wherein the signal generated by the detectable label correlates with the presence of gram positive bacteria, and wherein the unbound labeled antibody is removed prior to assessment of binding.

2. The method of claim 1, wherein the targeted ClfA is from gram positive bacteria including but not limited to *Staphylococci, Enterococci, Streptococci, Clostridium, Listeria*, or *Bacillus*.

3. The method of claim 2, wherein the test sample is a patient sample and the gram positive bacteria is *Staphylococcus* and the method further comprises correlating the presence of *Staphylococcus* in the test sample, wherein and diagnosing a patient with a staphylococcal infection.

4. A method of using a pharmaceutical composition for treating, preventing or reducing a gram positive bacterial infection in a patient comprising:

administering an effective amount of the pharmaceutical composition to the patient for decreasing the severity of gram positive bacteria-associated sepsis in the patient; delaying the onset of sepsis associated with gram positive bacterial infections in the patient; preventing the onset of sepsis associated with gram positive bacterial infections in the patient; reducing gram positive bacterial load in the bloodstream or heart in the patient; reducing gram positive bacterial agglutination and/or thromboembolic lesion formation in the patient; or preventing gram positive bacterial infections in the patient, wherein the pharmaceutical composition comprises an antibody that binds to a portion of a N3 fibrinogen binding site of Clumping factor A protein (ClfA), wherein the portion of the N3 fibrinogen binding site that the antibody binds to is selected from the group consisting of SEQ ID NO:15, SEQ ID NO:16, SEQ ID NO:17, and SEQ ID NO:18, and wherein the binding of the antibody to the N3 fibrinogen binding site reduces binding of fibrinogen to the ClfA.

5. The method of claim 4, further comprising the step of providing one or more antibiotics to the patient in addition to the pharmaceutical composition.

6. The method of claim 4, wherein the one or more antibiotics are selected from but not limited to penicillin G, oxacillin, vancomycin, flucloxacillin, amoxicillin, ampicillin, antipseudomonal penicillins, methicillin, nafcillin, cloxacillin, dicloxacillin, cephalosporins, carbapenems, imipenem, meropenem, ertapenem, doripenem, tetracyclines, macrolides, fluoroquinolones, trimethoprim/sulfamethoxazole (TMP/SMX), gentamicin, vancomycin, daptomycin, telavancin, cefazolin, mupirocin, teicoplanin, tetracyclines, minocycline, doxycycline, erythromycin, rifampin, clindamycin, linezolid, and aminoglycoside.

7. The method of claim 4, wherein the gram positive bacteria are *Staphylococcus*.

8. The method of claim 4, wherein the gram positive bacteria are *S. aureus*.

9. The method of claim 4, wherein the ClfA is from *S. aureus*.

10. The method of claim 4, wherein the gram positive bacteria include but are not limited to *Staphylococci, Enterococci, Streptococci, Clostridium, Listeria*, or *Bacillus*.

11. A composition comprising a peptide of *S. aureus* Clumping factor A protein (ClfA), wherein the peptide comprises a fibrinogen binding site and the peptide is SEQ ID NO:17.

* * * * *

SEQUENCE LISTING

```
<160> NUMBER OF SEQ ID NOS: 18

<210> SEQ ID NO 1
<211> LENGTH: 34
<212> TYPE: DNA
<213> ORGANISM: Artificial Sequence
<220> FEATURE:
<223> OTHER INFORMATION: Synthetic primer

<400> SEQUENCE: 1

gtaatgcatt aatagatcag aaaaatacaa gtat                              34


<210> SEQ ID NO 2
<211> LENGTH: 31
<212> TYPE: DNA
<213> ORGANISM: Artificial Sequence
<220> FEATURE:
<223> OTHER INFORMATION: Synthetic primer

<400> SEQUENCE: 2

ctgatctatt aatgcattac tatccgtatt t                                 31


<210> SEQ ID NO 3
<211> LENGTH: 34
<212> TYPE: DNA
<213> ORGANISM: Artificial Sequence
<220> FEATURE:
<223> OTHER INFORMATION: Synthetic primer

<400> SEQUENCE: 3

actttgagga tgtcactaat caggtgaata ttac                              34
```

<210> SEQ ID NO 4
<211> LENGTH: 31
<212> TYPE: DNA
<213> ORGANISM: Artificial Sequence
<220> FEATURE:
<223> OTHER INFORMATION: Synthetic primer

<400> SEQUENCE: 4
attagtgaca tcctcaaagt tttctggatt c 31

<210> SEQ ID NO 5
<211> LENGTH: 34
<212> TYPE: DNA
<213> ORGANISM: Artificial Sequence
<220> FEATURE:
<223> OTHER INFORMATION: Synthetic primer

<400> SEQUENCE: 5
aggatgtcac taatagtgtg cgtattacat tccc 34

<210> SEQ ID NO 6
<211> LENGTH: 31
<212> TYPE: DNA
<213> ORGANISM: Artificial Sequence
<220> FEATURE:
<223> OTHER INFORMATION: Synthetic primer

<400> SEQUENCE: 6
cacactatta gtgacatcct caaagttttc t 31

<210> SEQ ID NO 7
<211> LENGTH: 34
<212> TYPE: DNA
<213> ORGANISM: Artificial Sequence
<220> FEATURE:
<223> OTHER INFORMATION: Synthetic primer

<400> SEQUENCE: 7
ctttatatgg gtataactcg cgtataattt ggcg 34

<210> SEQ ID NO 8
<211> LENGTH: 31
<212> TYPE: DNA
<213> ORGANISM: Artificial Sequence
<220> FEATURE:
<223> OTHER INFORMATION: Synthetic primer

<400> SEQUENCE: 8
cgagttatac ccatataaag ttgaacgtaa a 31

<210> SEQ ID NO 9
<211> LENGTH: 25
<212> TYPE: DNA
<213> ORGANISM: Artificial Sequence
<220> FEATURE:
<223> OTHER INFORMATION: Synthetic primer

<400> SEQUENCE: 9
gaatattaca ttcgcaaatc caaat 25

<210> SEQ ID NO 10
<211> LENGTH: 26
<212> TYPE: DNA
<213> ORGANISM: Artificial Sequence
<220> FEATURE:
<223> OTHER INFORMATION: Synthetic primer

<400> SEQUENCE: 10
gatttggatt tgcgaatgta atattg 26

<210> SEQ ID NO 11
<211> LENGTH: 29
<212> TYPE: DNA
<213> ORGANISM: Artificial Sequence
<220> FEATURE:
<223> OTHER INFORMATION: Synthetic primer

<400> SEQUENCE: 11
gttataccca gttaaagcag aacgtaaag 29

<210> SEQ ID NO 12
<211> LENGTH: 29
<212> TYPE: DNA
<213> ORGANISM: Artificial Sequence
<220> FEATURE:
<223> OTHER INFORMATION: Synthetic primer

<400> SEQUENCE: 12
ctttacgttc tgctttaact gggtataac 29

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
gaatataatt gcgcgctcta tgtc 24

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
gacatagagc gcgcaattat attc 24

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 15

Ile Ala Xaa Val Xaa Thr
1 5

<210> SEQ ID NO 16
<211> LENGTH: 7
<212> TYPE: PRT
<213> ORGANISM: Artificial Sequence
<220> FEATURE:

-continued

<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 16

Gln Gln Xaa Thr Ser Ile Leu
1 5

<210> SEQ ID NO 17
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 17

Xaa Thr Asn Ser Val Asn Ile Thr Phe Pro Xaa Xaa Xaa Gln Xaa Leu
1 5 10 15

Xaa Glu Xaa Asn Thr Pro Asp Asp
20

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 18

Tyr Xaa Tyr Xaa Xaa Xaa Ile Xaa Trp
1 5